(12) United States Patent
Enk

(10) Patent No.: US 7,204,248 B2
(45) Date of Patent: Apr. 17, 2007

(54) FIBEROPTIC NEBULIZER

(75) Inventor: Dietmar Enk, Coesfeld (DE)

(73) Assignee: Cook Critical Care Incorporated, Bloomington, IN (US)

( * ) Notice: Subject to any disclaimer, the term of this patent is extended or adjusted under 35 U.S.C. 154(b) by 680 days.

(21) Appl. No.: 10/361,366

(22) Filed: Feb. 10, 2003

(65) Prior Publication Data

US 2004/0154617 A1  Aug. 12, 2004

Related U.S. Application Data

(63) Continuation-in-part of application No. 10/259,999, filed on Sep. 27, 2002, now abandoned.

(51) Int. Cl.
*A61M 11/00* (2006.01)
*A61M 15/00* (2006.01)
*A61M 16/00* (2006.01)

(52) U.S. Cl. .......... 128/203.12; 128/200.14; 128/203.25

(58) Field of Classification Search .......... 128/200.14, 128/203.12, 200.21, 200.26, 207.14, 207.15, 128/912, 203.15, 203.16, 204.18, 203.22, 128/204.11, 204.12, 203.14; 239/335, 338, 239/340, 346, 347, 348, 369
See application file for complete search history.

(56) References Cited

U.S. PATENT DOCUMENTS

| | | | |
|---|---|---|---|
| 2,003,087 A * | 5/1935 | Lynger | 239/347 |
| 3,809,080 A | 5/1974 | Deaton | |
| 4,150,071 A | 4/1979 | Pecina | |
| 4,423,725 A | 1/1984 | Baran et al. | |
| 4,461,293 A * | 7/1984 | Chen | 128/204.23 |
| 5,016,614 A | 5/1991 | Macallister | |
| 5,072,726 A | 12/1991 | Mazloomdoost et al. | |
| 5,452,714 A * | 9/1995 | Anderson et al. | 128/205.11 |
| 5,461,695 A | 10/1995 | Knoch | |
| 5,571,071 A | 11/1996 | Shapiro | |
| 5,599,297 A | 2/1997 | Chin et al. | |
| 5,776,052 A | 7/1998 | Callahan | |
| 5,810,786 A | 9/1998 | Jackson et al. | |
| 5,813,401 A * | 9/1998 | Radcliff et al. | 128/205.24 |
| 6,021,776 A | 2/2000 | Allred et al. | |
| 6,086,559 A | 7/2000 | Enk | |
| 6,106,458 A | 8/2000 | Ha | |
| 6,196,225 B1 | 3/2001 | Allgeyer | |
| 6,221,007 B1 | 4/2001 | Green | |
| 6,526,976 B1 * | 3/2003 | Baran | 128/207.14 |

FOREIGN PATENT DOCUMENTS

| | | |
|---|---|---|
| FR | 2 746 626 | 10/1997 |
| WO | WO 97/47345 | 12/1997 |

OTHER PUBLICATIONS

International Search Report, dated Jan. 26, 2004, for corresponding international application PCT/EP03/10546.

* cited by examiner

*Primary Examiner*—Teena Mitchell
*Assistant Examiner*—Amadeus Lopez
(74) *Attorney, Agent, or Firm*—Brinks Hofer Gilson Lion

(57) ABSTRACT

A nebulizer uses air or preferably oxygen to aerate and transport an anesthetic for providing topical anesthesia to the airway passages of a patient undergoing analysis or treatment by any of several medical instruments used to traverse the airway passages. The nebulizer is preferably applied in connection with fiberoptical diagnostic and therapeutic instruments, such as bronchoscopes, endoscopes and laryngoscopes, and many variations of these instruments. Other liquid, aerosol, and gaseous drugs may also be administered with the nebulizer.

17 Claims, 6 Drawing Sheets

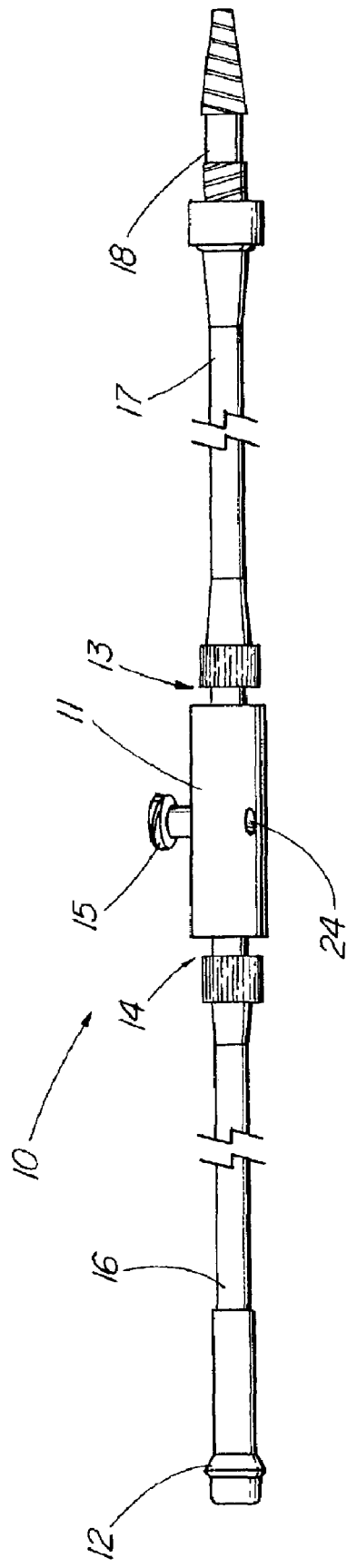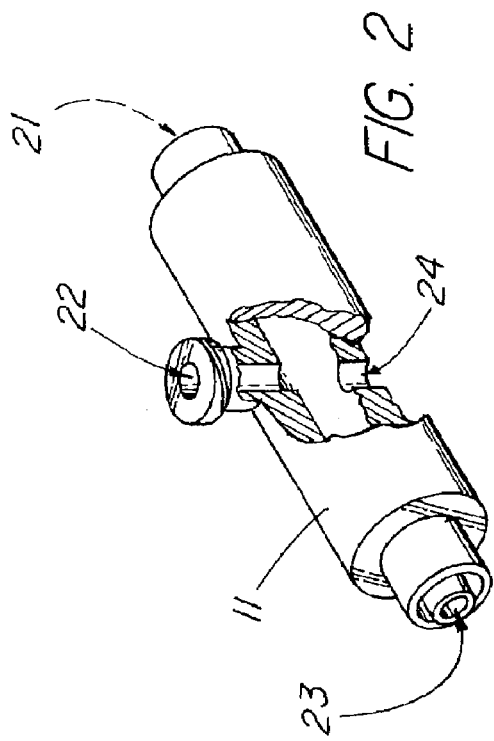

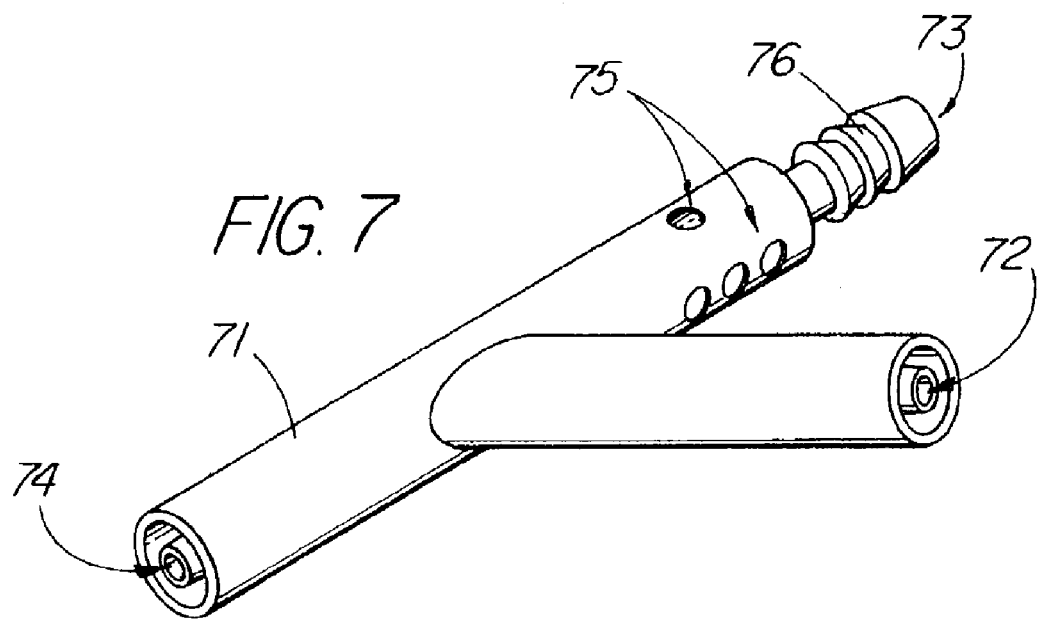
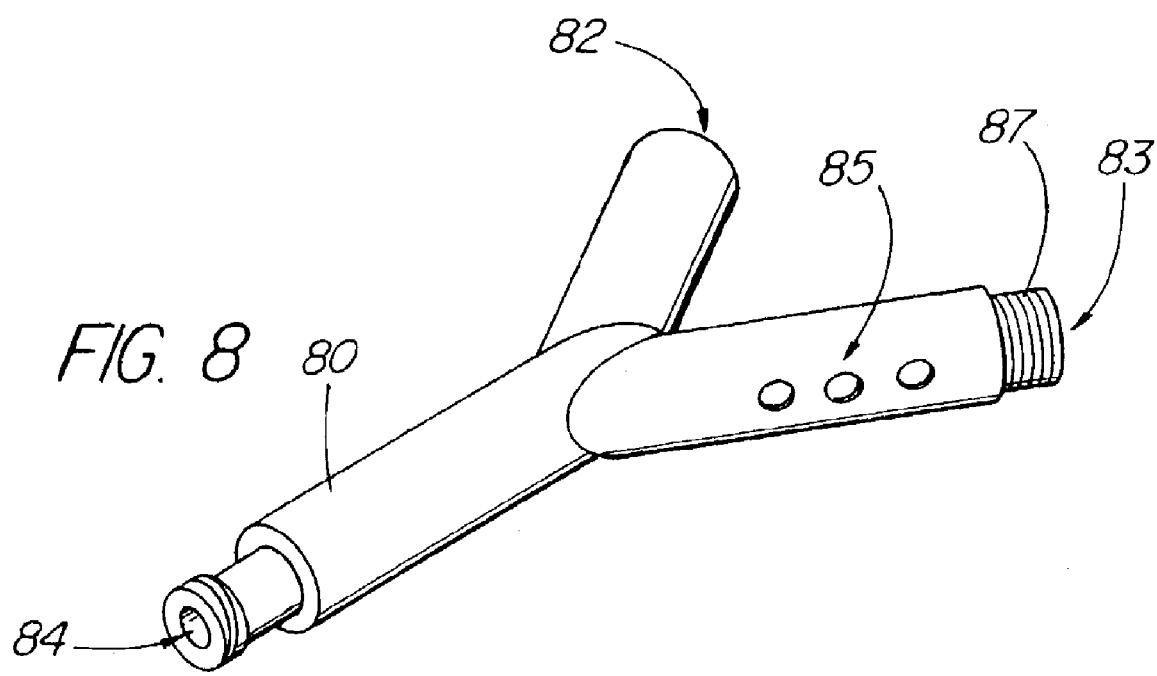

FIBEROPTIC NEBULIZER

This application is a continuation-in-part, and claims priority to and the benefit of U.S. patent application Ser. No. 10/259,999, filed Sep. 27, 2002, now abandoned, which is hereby incorporated by reference.

FIELD OF THE INVENTION

This invention introduces a device for delivering medication or an anesthetic to the upper airway (nose, mouth, throat), larynx, trachea, and bronchial stem of a patient when undergoing analysis or treatment by any of several instruments used to traverse the airway passages of a patient.

BACKGROUND OF THE INVENTION

As physicians perform more and more surgery in a minimally-invasive manner, the techniques used to perform the surgery need to be improved. Among the primary motives are improvement of the procedure itself and the ease of performing a procedure so that physicians may more easily learn and execute the procedure. Patient comfort during and after the procedure should also be improved so that there are minimal side effects and after effects.

There are many procedures that require instruments to traverse the upper airway (nose, mouth, throat) of a patient, some extending all the way down the throat to the pulmonary or digestive system. Such procedures are usually performed with the patient awake, but often with "conscious sedation." This technique may involve several different kinds of medications, including those to numb the passageways, another to help control coughing, and perhaps another to keep the patient relaxed. All of these procedures have in common the traversal of the throat, and all of them require some control of the gag reflex of the patient as the instrument proceeds through the passageway. Proper and facile advancement of the instrument through the airway is important to insure sufficient respiration during the entire period of the procedure.

Several techniques have been used to provide topical anesthesia for endotracheal intubation in a patient who is awake. One possible device is revealed in U.S. Pat. No. 5,072,726. This device uses high-frequency jet ventilation and requires an infusion pump to vaporize a local anesthetic. Another device, revealed by U.S. Pat. No. 5,571,071 is directed to delivery of a local anesthetic mist by a portion of a laryngoscope. This device and the procedure for using it supply virtually no air or oxygen to the patient during the delivery of the local anesthetic, and there does not appear to be a controlled delivery of the local anesthetic during the use of the device.

In one presently-known but unsatisfactory method, a physician injects 2–3 ml of a local anesthetic through the working channel of a flexible fiberscope into the airway passage, with or without an air/oxygen assist. The solution does not vaporize or atomize, and instead exits with a splash into the airway passage, typically irritating the patient. Subsequent coughing or choking of the patient (or both) may impede at least the fiberoptical view or orientation, but may even result in trauma caused by the fiberscope. The local anesthetic is thus not well-controlled nor is it well-distributed. Repeated administration due to insufficient topical anesthesia during endoscopy and intubation may result in overexposure of the patient to the local anesthetic.

None of these devices or techniques provides a simple, quick, and efficient way to aerate and deliver a local anesthetic in a fine mist to the airway passages. In addition, it would be beneficial to the patient to limit the amount of local anesthetic, in order to avoid any possible toxicity or adverse reactions. The present invention is directed at correcting these deficiencies in the prior art. What is needed is a relatively simple device that allows quick and efficient application of a small amount of local anesthetic resulting in sufficient topical anesthesia.

SUMMARY

One embodiment of the invention is a drug nebulizer. The nebulizer comprises a three-branched fitting having a first inlet, a second inlet, an outlet, and at least one orifice, wherein the first inlet is configured for receiving a gas selected from the group consisting of air and oxygen, the second inlet is configured for receiving a drug, and the at least one orifice is configured for flow control of the nebulizer. Another embodiment of the invention is a method of administering a drug to an airway of a patient. The method comprises connecting a nebulizer to an instrument for traversing the airway of the patient, and flowing a gas selected from the group consisting of air and oxygen to the nebulizer. The method also includes blocking at least one orifice of the nebulizer and introducing the drug into the nebulizer.

The nebulizer may be used to deliver local anesthetics to the airway of a patient. The nebulizer is not limited to such drugs, however, and may be used to administer any suitable drug or medication, liquid or gaseous, to the airway of a patient. Other systems, methods, features, and advantages of the invention will be or will become apparent to one skilled in the art upon examination of the following figures and detailed description. All such additional systems, methods, features, and advantages are intended to be included within this description, within the scope of the invention, and protected by the accompanying claims.

BRIEF DESCRIPTION OF THE FIGURES

The invention may be better understood with reference to the following figures and detailed description.

FIG. 1 is a plan view of an embodiment.

FIG. 2 is a perspective view of the embodiment of FIG. 1.

FIGS. 7–8 are perspective views of alternate embodiments.

DETAILED DESCRIPTION OF THE PRESENTLY PREFERRED EMBODIMENTS

The present invention meets these needs with a nebulizer that nebulizes or atomizes a small amount of a local anesthetic solution with a stream of air or preferably oxygen. The mixed stream of oxygen and nebulized local anesthetic then enters a short length of tubing which is connected to a working portion of an optical diagnostic or therapeutic instrument, such as a flexible bronchoscope. A flexible bronchoscope is a fiberoptical instrument that can be used to examine the bronchial stem of the lung and to obtain samples for testing. A flexible bronchoscope typically consists of a coherent glass fiber bundle covered by a front lens, one or two light bundles, and wires to control the highly flexible tip. A flexible bronchoscope usually has a working channel so that special instruments may be passed through the working channel to reach inside the airway passages of a patient. The working channel can also be used to suck mucus out of the airway passages and to administer air or preferably oxygen to the patient. Other instruments besides a flexible bronchoscope may also be used in combination with the embodiment.

The nebulizer is connected to a source of air or preferably oxygen and to an instrument for traversing the airway of a patient, e.g. a flexible bronchoscope. The nebulizer is operated in three primary modes, a standby mode for delivering no air or oxygen to the patient, a mode for delivering a low flow of air or preferably oxygen at low pressure, and a nebulizing mode for delivering high flow of air or preferably oxygen at high pressure.

In the standby mode (no syringe connected to the second inlet and at least one orifice released), no flow or at most a minimal flow of air or preferably oxygen at very low pressure is applied to the patient. In the low flow mode (syringe connected to the second inlet and at least one orifice released), some air or preferably oxygen flows to the patient, e.g. through the working channel of a flexible bronchoscope. While a continuous flow of air through the working channel is effective in reducing contamination of the front lens by mucus, a continuous flow of oxygen also maintains or reestablishes sufficient oxygenation of an awake, spontaneously breathing patient during the diagnostic or therapeutic procedure.

In the nebulizing mode (syringe connected to the second inlet and orifice or orifices blocked), the full flow selected from a source of air or preferably oxygen, e.g. 9–10 liters/min., delivers a small amount of a local anesthetic as a fine mist to the patient. In one example, 1 ml of a 2% lidocaine solution is nebulized and delivered to the patient. A high flow of air, or preferably oxygen, causes a small amount of a local anesthetic solution to break into small droplets, that is, to nebulize. Since the impact of these small droplets is hardly noticeable for the patient, and the efficient distribution of the local anesthetic results in sufficient topical anesthesia, discomfort to the patient can be minimized during traversal of the airway, e.g. by a flexible bronchoscope. Other medications or drugs may also be delivered in this manner.

The nebulizing mode can be used not only for nebulizing a local anesthetic, but also for so-called "jet ventilation" through the working channel of a flexible bronchoscope. This can be a life-saving use in a situation of complete upper airway obstruction, when the tip of the flexible bronchoscope is in a tracheal position, but it is impossible to advance the endotracheal tube over the bronchoscope. If this occurs, the patient can be oxygenated efficiently and ventilated at a reduced level by alternately suctioning through the working channel and controlling the "injection" of oxygen by blocking the orifice intermittently.

FIG. 1 depicts a first embodiment of a nebulizer assembly 10 ready for connection to a flexible bronchoscope (not shown). The assembly 10 includes a local anesthetic nebulizer 11, an inlet and connector for air or preferably oxygen in 13, a main outlet and connector for air or preferably oxygen out 14, and an inlet and connector for the local anesthetic solution 15. The assembly 10 also includes an air or preferably oxygen inlet tubing 17 and a connector 18 to a source of air or preferably oxygen (not shown). Outlet tubing 16 with connector 12 leads to a matching connector on an optical or therapeutic instrument, such as a flexible bronchoscope. There is also at least one orifice 24 for controlling the flow of air or oxygen.

A closer view of the nebulizer is depicted in FIG. 2. The local anesthetic nebulizer 11 has a first inlet 21, a main outlet 23 opposite the first inlet 21, and a second inlet 22 midway between the first inlet 21 and the main outlet 23. Together, the three ports resemble a tee-shaped pipe fitting. There is also an orifice 24 opposite the second inlet 22. In this embodiment, air or preferably oxygen enters first inlet 21 and leaves via main outlet 23. The local anesthetic is administered via the second inlet 22 while an operator briefly covers orifice 24 to insure that all air or preferably oxygen and local anesthetic leaves via main outlet 23. As depicted in FIG. 2, the local anesthetic nebulizer 11 may have connectors integrally molded into the nebulizer for the second inlet 22 and the first inlet 21 and main outlet 23 for the air or preferably oxygen.

The nebulizer thus may have four ports, two inlets and two outlets. The first inlet is preferably for oxygen (it may also be used for air) and the second inlet is adapted to receive a syringe for delivering the local anesthetic. The main outlet goes to a working channel in an optical diagnostic or therapeutic instrument. There is also a secondary outlet via the at least one orifice. The first inlet is connected to a source of air or preferably oxygen. The second inlet is connected to a syringe, or otherwise may be blocked, e.g. by hand or by a fitting. The main outlet is open at all times. The secondary outlet or orifice is open, and air or preferably oxygen will flow into the nebulizer, and out of both outlets. Therefore, if the air or preferably oxygen flow is constant, a patient will receive a reduced amount of air or preferably oxygen during the time that the secondary outlet is open, because some of the air or preferably oxygen will flow from the secondary outlet and will not flow solely from the main outlet to the patient. In a preferred embodiment, the tee-shaped pipe fitting has three ports that are about 2.5 mm diameter as described. If there is one orifice, it is about 2 mm in diameter, and may be located opposite the second inlet for the local anesthetic. The cross-sectional area of the orifice may be equal to, but is preferably less than the cross-sectional area of the main outlet. If there is more than one orifice, they may be from about 1.0 mm in diameter to about 2.5 mm in diameter.

When it is time to apply the local anesthetic to the patient's airway via either embodiment of the nebulizer, the air or preferably oxygen flow is begun, and a syringe is placed into the second inlet of the nebulizer. The secondary outlet, which may be one orifice or more than one orifice, is blocked, thus forcing all air or preferably oxygen through the main outlet. The local anesthetic is then forced from the syringe into the air or preferably oxygen stream, and is nebulized or atomized by the high flow of air or preferably oxygen. The mixture of air or preferably oxygen and local anesthetic proceeds down the working channel of an optical diagnostic or therapeutic instrument, such as a flexible bronchoscope. The local anesthetic is thus immediately applied to the portion of the airway just outside the working channel, with some portion going downstream. The air or preferably oxygen flow typically has to be reduced to a lower level afterwards by unblocking the secondary outlet, which may be one orifice or more than one orifice. More local anesthetic may be applied in subsequent nebulizing steps. In one embodiment, about 1 ml of a 2% lidocaine solution delivered from a 1 ml syringe is applied instantaneously by nebulizing the local anesthetic in a stream of oxygen flowing at about 10 liters/min. The use of smaller amounts of local anesthetic may be beneficial to the patient, who may thus have a smaller risk of suffering from systemic toxicity of the anesthetic.

It should be noted that the local anesthetic nebulizer is also useful for procedures other than mere intubation. The local anesthetic nebulizer provides comfort for the patient during introduction of any instrument into the upper airway or passage of any instrument through the upper airway. For instance, bronchoscopes are often used for biopsy or other therapeutic procedures, and the local anesthetic may even be administered for introduction of a bronchoscope into the bronchial stem.

Figure 3:
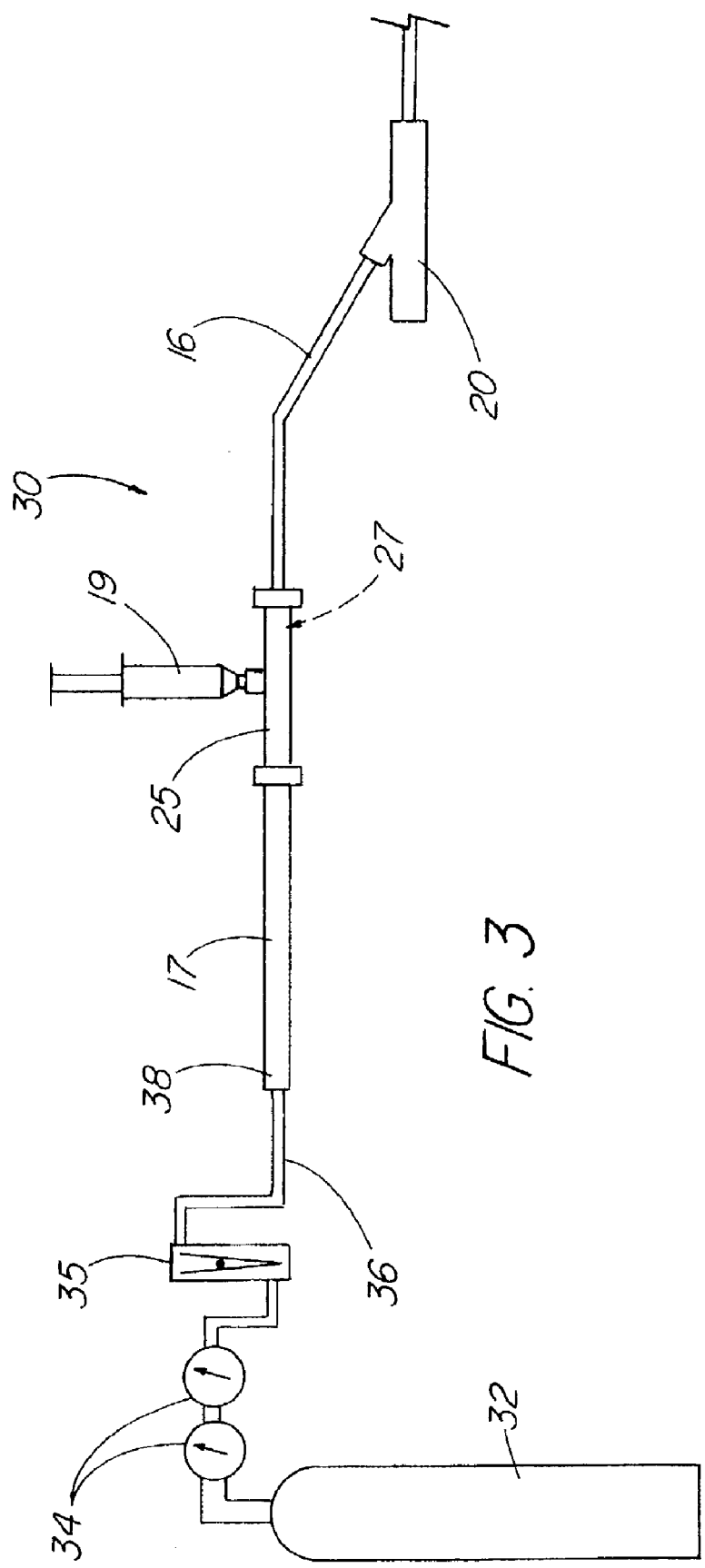
FIG. 3 is a diagrammatical view depicting an embodiment with the orifice downstream of the syringe.

A more comprehensive view of the situation is depicted in FIG. 3. A combination 30 of the nebulizer 25 and a bronchoscope 20 is connected to a source of regulated oxygen 32 and is ready for use in a patient (not shown). In this embodiment, the nebulizer 25 has an orifice 27 placed downstream of the syringe 19, rather than directly opposite as in the previous embodiment. A source of oxygen 32, such as a 1 A cylinder or other source is regulated by a pressure regulator 34. There is a flowmeter 35 connected in series to tubing 36 to deliver the oxygen. The flowmeter 35 is desirably close to the bronchoscope 20 and patient, so that the flow of oxygen may be observed and readily adjusted as desired. Flowmeter 35 may be a rotameter type of flowmeter or any other flowmeter suitable for oxygen and use on human patients.

In one embodiment, a pressure relief fit may be achieved by snugly fitting smaller tubing 36 into larger tubing 17, so that if a downstream block occurs, the tubing connection will break far apart from any person without any risk of injury for the patient, the physician, and the assisting nurse. Inlet tubing 17 and outlet tubing 16 connect to the nebulizer 25 as previously discussed, and outlet tubing 16 then connects to a bronchoscope 20. In this example, syringe 19 with a small amount of a local anesthetic solution is connected to the nebulizer 25 and is ready for injection. The tubing between the source of air or preferably oxygen and the local anesthetic nebulizer may be any tubing suitable for the use of air or preferably oxygen in life-preserving or hospital situations. Plastic tubing of a few millimeters diameter that will reliably deliver the air or preferably oxygen without confusion of the identity of the gas is recommended. The inlet and outlet tubing will ideally be flexible, kink-resistant and non-compliant. It should hold its shape during delivery of the local anesthetic to the patient. This will allow the anesthetic to be distributed in a relatively uniform and effective manner.

Figure 4:
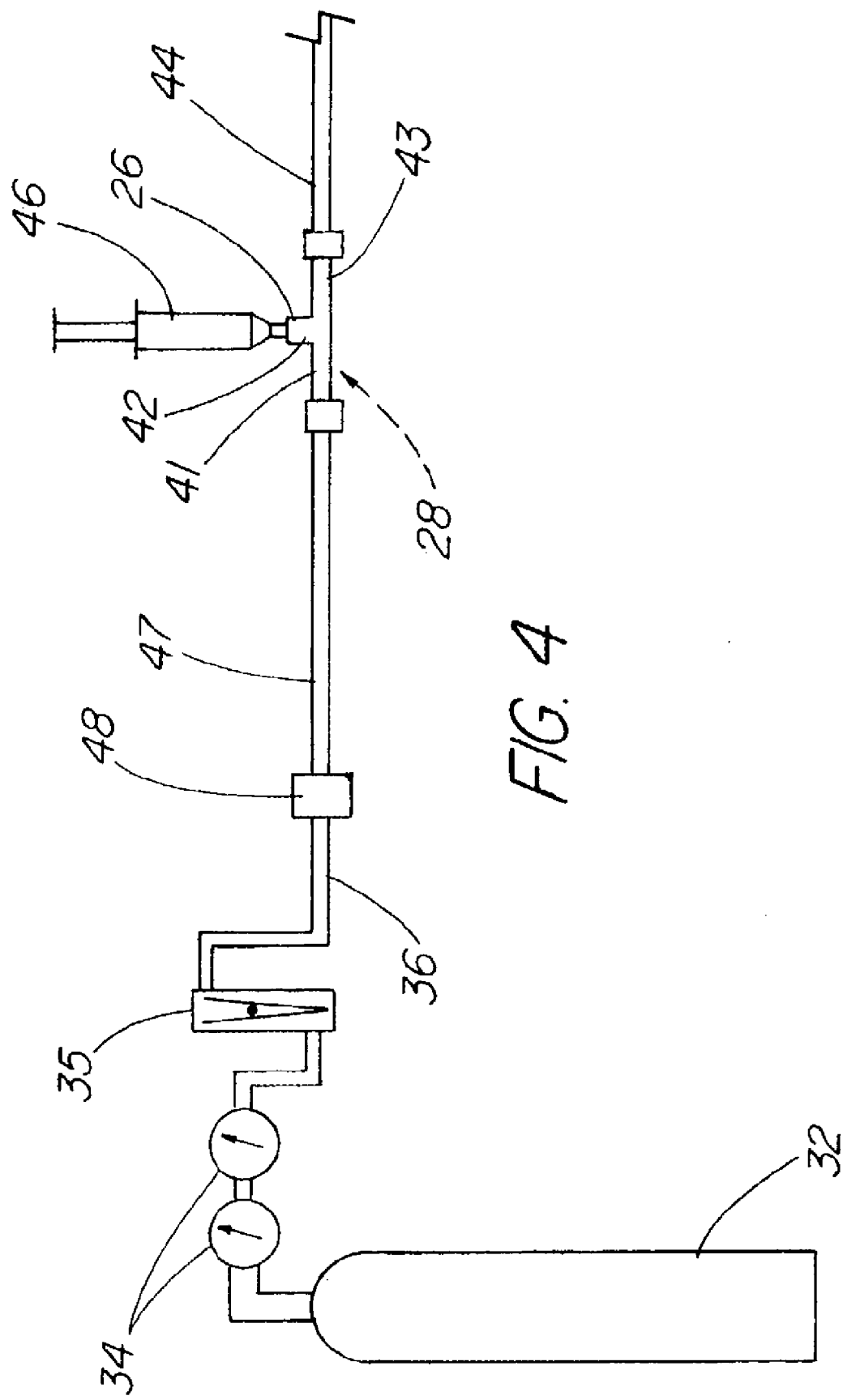
FIG. 4 is a diagrammatical view depicting another embodiment with the orifice upstream of the syringe.

FIG. 4 depicts another embodiment of the nebulizer. In FIG. 4, a nebulizer 26 with three connectors and at least one orifice 28 is connected via male Luer outlet connector 43 to tubing 44 for connecting to a bronchoscope (not shown). The nebulizer 26 is connected via female Luer inlet connector 42 to a syringe 46, and is also connected via male Luer connector 41 to inlet tubing 47. Orifice 28 is placed upstream of the syringe 46 in this embodiment. A source of oxygen 32 is controlled through a pressure regulator 34 and a flowmeter 35, delivering the oxygen via tubing 36 to a pressure relief connection 48. Pressure relief connection 48 connects to inlet tubing 47 to supply oxygen to nebulizer 26. The nebulizer works as described above.

Figure 5:
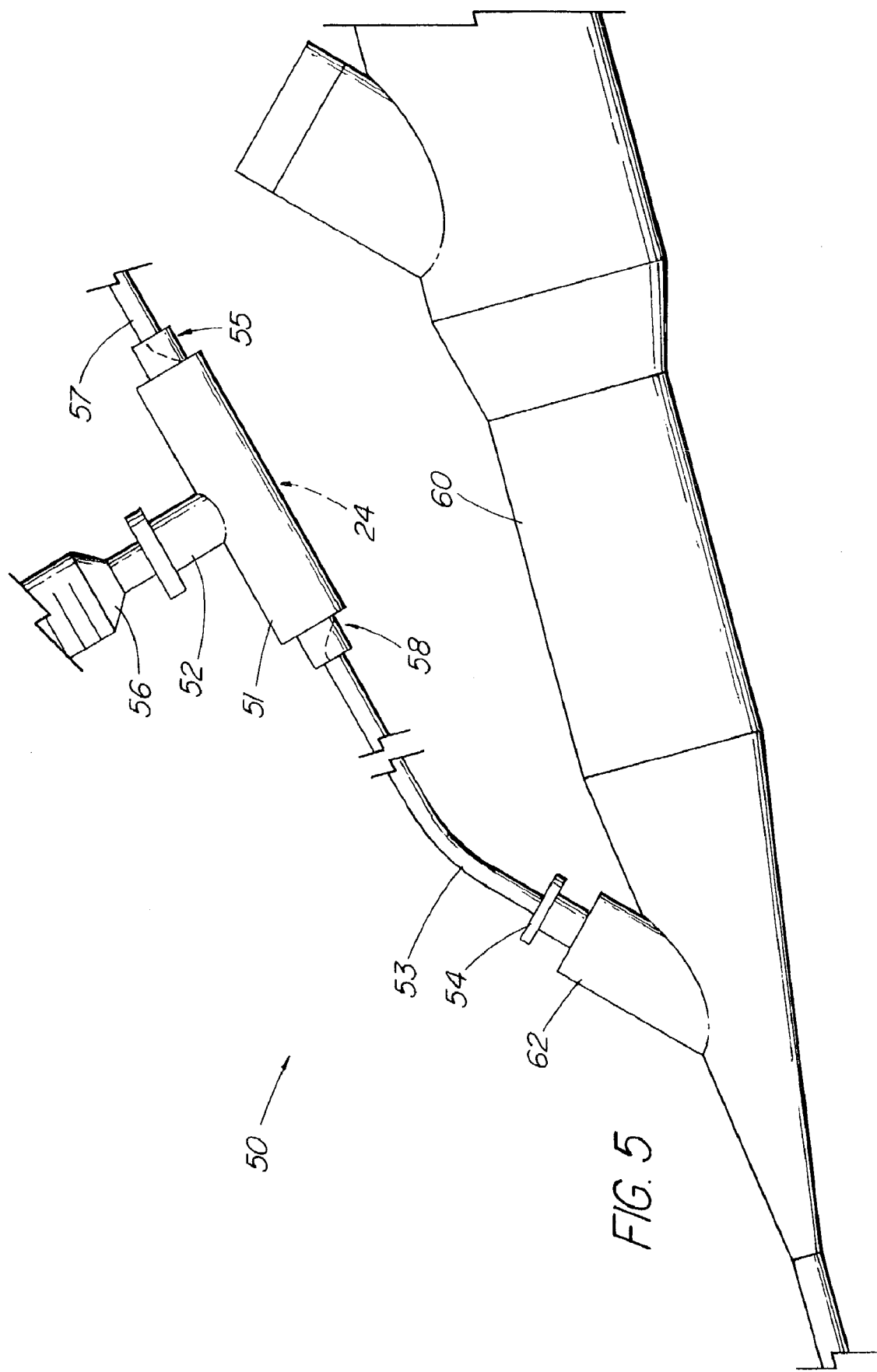
FIG. 5 is a plan view of a connection between the nebulizer and a bronchoscope.
Figure 6:
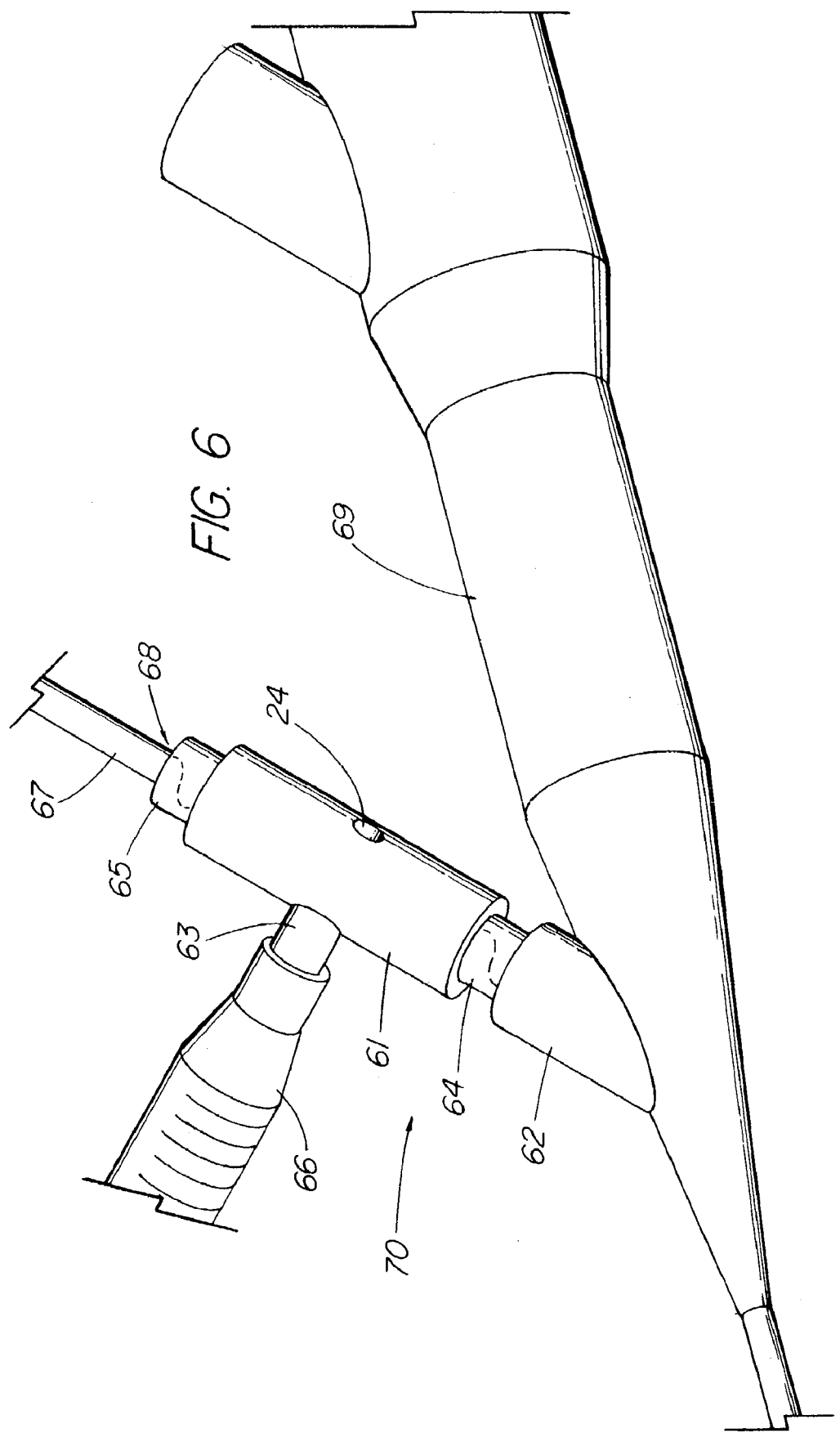
FIG. 6 is a perspective view of an alternate connection to a bronchoscope.

FIGS. 5 and 6 depict alternate connections for a nebulizer as it would be assembled to a bronchoscope to receive oxygen and local anesthetic and to deliver oxygen and local anesthetic to a patient. FIG. 5 depicts a preferred embodiment of a combination 50 of a bronchoscope 60 and nebulizer 51. The nebulizer 51 resembles a tee-shaped pipe fitting, and has an inlet connector 55, such as a Luer connector, for connecting to a source of oxygen (not shown) via tubing 57. The nebulizer also has a male Luer outlet connector 58 for connecting to an outlet tubing 53. The opposite end of the outlet tubing 53 and its connector 54 mate to a mating connector 62 on bronchoscope 60. The nebulizer 51 also has a female Luer inlet connector 52 for connecting to a syringe 56 for delivering local anesthetic. There is also at least one orifice 24 in the nebulizer 51 opposite the female Luer inlet connector 52 to control flow to the patient.

FIG. 6 depicts another embodiment of a combination 70 of a bronchoscope 69 and nebulizer 61, without connecting tubing between the male Luer outlet connector 64 and the bronchoscope 69. Nebulizer 61 resembles a tee-shaped pipe fitting, and connects via male Luer inlet connector 65 to a source of oxygen (not shown) via inlet tubing 67 and connector 68. Nebulizer 61 also connects to a syringe 66 for delivering a local anesthetic via female Luer inlet connector 63 on nebulizer 61. Nebulizer 61 has a male Luer outlet connector 64 for connecting to a mating connector 62 on the bronchoscope 69. There is also an orifice 24 in the nebulizer 61 opposite the female Luer inlet connector 63 for flow control to the patient.

When the much-better controlled anesthetic reaches the mucosa of the airway as a fine spray, it noticeably improves patient comfort. In clinical endoscopy conducted on 50 patients with a bronchoscope, anesthesiologists administered smaller doses of lidocaine via the nebulizer, while rating the coughing of the patients as exceptionally low during both endoscopy and spraying. Patients assessed their own comfort as about 2.6 on a 10-point scale (0 is excellent, 10 is awful), while the anesthesiologists rated conditions for the procedure at about 1.2. These are highly favorable results.

Nebulizer embodiments according to the present invention are not limited to tee-shapes, nor are they limited to having a single orifice for flow control. In other embodiments, the shape of the nebulizer embodiment may be angled, as in a bent "T" or a "Y." In other embodiments, there may be a series of orifices, rather than a single orifice. Further examples are depicted in FIGS. 7 and 8. FIG. 7 is a perspective view of an alternate embodiment of the nebulizer, in which the nebulizer is in the general shape of an angled "T." Nebulizer 71 is a three-branched fitting, including an inlet 72 for a drug, preferably a liquid drug, an inlet 73 for air or preferably oxygen, and an outlet 74. The nebulizer 71 has not one orifice but several orifices 75, preferably upstream of the inlet 72 for a drug. By having more than one orifice, the chance that all orifices 75 will be accidentally blocked is reduced. Only when all orifices 75 are blocked is the full flow of air or preferably oxygen from the inlet 73 for air or preferably oxygen available at outlet 74 and thus to instruments or a patient downstream from the nebulizer. In this embodiment, the orifices 75 are not in line, but rather are spaced so that more than one finger, at least two fingers or a hand, is required to close all the orifices 75 at once. Thus, in the embodiment of FIG. 7, the orifices 75 may be closed by a palm of the hand and a thumb, but may not be closed by merely a finger, e.g. a finger of an anesthesiologist operating the nebulizer.

Inlet 73, with a barbed connector 76, is preferably configured to receive a gas. The tubing that delivers the air or preferably oxygen for the patient to inlet 73 is preferably equipped with a mating fitting for connecting to inlet 73. Inlet 72, in this embodiment a female Luer connector, is preferably configured to receive a drug to be administered through nebulizer 71. If the drug is a liquid, then inlet 72 preferably has a connector for mating with a syringe or other drug delivery device. If the drug is an aerosol or is gaseous, inlet 72 preferably has a connector for mating with the source of the aerosol or gaseous drug. The outlet 74 of nebulizer 71, in this case a female Luer connector, should be configured to mate with the bronchoscope or other diagnostic or therapeutic instrument.

FIG. 8 is another embodiment of a nebulizer 80, in which the nebulizer is in the general shape of a "Y." Nebulizer 80 has three branches, including a branch and inlet 82 for a drug, a branch and inlet 83 for air or preferably oxygen, and a third branch 84 as an outlet for the nebulizer. In the embodiment of FIG. 8, inlet 82 is in the form of a female Luer connector and outlet 84 is in the form of a male Luer connector. Inlet 83 is in the form of male pipe threads 87 for connection to a source of air or preferably oxygen, such as a female threaded quick-connect fitting. Nebulizer 80 has a plurality of orifices 85, preferably upstream of the branch point for the drug. In this embodiment, all the orifices 85 may be closed with deliberate effort by a single finger. The embodiments shown in FIGS. 7–8, and their equivalents, are intended to add a safety feature to the nebulizer, if the air or preferably oxygen supply is at too high a pressure level. Of course, more than one orifice may also be used in the straight "T" shaped nebulizer embodiment. The nebulizers have in common the three-branched configuration.

The tubing for the air or preferably oxygen is desirably made of medical-grade plastic or elastomer, such as polyurethane or silicone, but may be made of other medical-grade material as well, so long as it is safe for air or preferably oxygen, and it is compatible with the drug (for at least a very brief period). The size of the tubing must be sufficient to conveniently flow the desired amount of air or preferably oxygen. 9.5 Fr standard-wall tubing (3.15 mm outer diameter, 1.75 mm inner diameter) has worked well. Tubing with another diameter may be used instead.

The connectors between the nebulizer, the tubing, the air or preferably oxygen source, the fiberoptical instrument, and the syringe may be any convenient medical-grade connectors, such as Luer connectors. Such connectors are typically made of nylon or PVC (polyvinyl chloride). Any other material compatible with the air or preferably oxygen and the local anesthetic may be used. The nebulizer itself may preferably be made of plastic, such as PVC. Since the nebulizer is meant for one-time use (for a single patient), the cost is desirably kept low. While PVC has been found acceptable, any other plastic or material compatible with the air or preferably oxygen and the drug to be administered may be used.

Of course in using the nebulizer described above, any of the several improvements may be used in combination with others features, whether or not they were explicitly described as such. Various embodiments of the invention have been described and illustrated. However, the description and illustrations are by way of example only. Other embodiments and implementations are possible within the scope of this invention and will be apparent to those of ordinary skill in the art. For instance, the procedures above have primarily described flexible fiberscopes, such as bronchoscopes, used in combination with the nebulizer. Endoscopes or laryngoscopes of many kinds may also be used. In addition, the nebulizer may be used for emergency ventilation, and may be combined with medical equipment that traverses the upper airway of a patient and extends into and beyond the throat. Thus, the application of the nebulizer is not limited to topical anesthesia, but may be used to nebulize and deliver any drug or medication that may be useful in treating or diagnosing the patient. Therefore, the invention is not limited to the specific details, representative embodiments, and illustrated examples in this description. Accordingly, the invention is not to be restricted except as necessitated by the accompanying claims and their equivalents.

What is claimed is:

1. A nebulizer for delivering a drug to a patient, comprising:
   a three-branched fitting having a first inlet, a second inlet, a primary outlet, and a secondary outlet comprising at least one orifice;
   wherein the first inlet is configured for receiving a gas selected from the group consisting of air and oxygen, the second inlet is configured for receiving the drug, the respective first and second inlets being arranged such that said gas and drug are capable of mixing within a passageway of said fitting to form a nebulized flow for delivery through the primary outlet, and the secondary outlet is configured for flow control of the nebulizer.

2. The nebulizer of claim 1, wherein the second inlet is configured for receiving a drug selected from the group consisting of a liquid, an aerosol, and a gaseous drug.

3. The nebulizer of claim 1, further comprising a syringe connected to the second inlet and tubing connected to at least one of the first inlet and the primary outlet.

4. The nebulizer of claim 1, further comprising a first length of tubing having a first diameter connected to the first inlet and a second length of tubing having a second diameter connected to the first length of tubing and a gas source.

5. The nebulizer of claim 1, further comprising a piece of tubing and an over-pressure relief, the piece of tubing connected to the first inlet, and the overpressure relief connected to the piece of tubing.

6. The nebulizer of claim 1, wherein a cross-sectional area of the secondary outlet is equal to or less than a cross-sectional area of the primary outlet.

7. The nebulizer of claim 1, wherein the secondary outlet is from about 1.0 mm to about 2.5 mm in diameter.

8. The nebulizer of claim 1, wherein the secondary outlet is placed opposite the second inlet.

9. The nebulizer of claim 1, wherein the secondary outlet is placed upstream of the second inlet.

10. The nebulizer of claim 1, wherein the fitting has a shape selected from the group consisting of a "T", a "Y", and a bent "T."

11. The nebulizer of claim 1, wherein at least one of the first inlet, the second inlet, and the primary outlet is a Luer connector.

12. A combination of the nebulizer of claim 1, a controller for controlling a flow of gas to the first inlet, a flowmeter in series with the controller, and tubing connecting the controller to the nebulizer.

13. A combination of the nebulizer of claim 1 and an optical diagnostic or therapeutic instrument having an airway connected to the primary outlet of the nebulizer, the optical instrument selected from the group consisting of flexible fiberscopes, endoscopes, and laryngoscopes.

14. The nebulizer of claim 1, wherein the second inlet is configured for receiving a liquid drug.

15. The nebulizer of claim 1, wherein the secondary outlet is configured and arranged relative to the first inlet, second inlet and primary outlet for enhancing flow through the nebulizer upon a blockage of said secondary outlet, and for reducing a flow through the nebulizer when said secondary outlet is unblocked.

16. The nebulizer of claim 1, wherein the secondary outlet comprises a plurality of orifices.

17. The nebulizer of claim 16, wherein said plurality of orifices are arranged in a non-linear orientation.

* * * * *